US012584883B2

(12) United States Patent
Keyser et al.

(10) Patent No.: US 12,584,883 B2
(45) Date of Patent: Mar. 24, 2026

(54) NANOPORE FUNCTIONALITY CONTROL

(71) Applicant: CAMBRIDGE ENTERPRISE LIMITED, Cambridge (GB)

(72) Inventors: Ulrich Keyser, Cambridge (GB); Nicholas Bell, Cambridge (GB); Tim Liedl, Munich (DE); Marc Ablay, Unterhaching (DE); Caterina Ducati, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 1341 days.

(21) Appl. No.: 17/211,564

(22) Filed: Mar. 24, 2021

(65) Prior Publication Data

US 2021/0341421 A1 Nov. 4, 2021

Related U.S. Application Data

(63) Continuation of application No. 16/404,164, filed on May 6, 2019, now Pat. No. 10,983,091, which is a
(Continued)

(30) Foreign Application Priority Data

Dec. 6, 2011 (GB) ..................................... 1120910

(51) Int. Cl.
*G01N 27/447* (2006.01)
*C12Q 1/6825* (2018.01)
*C12Q 1/6869* (2018.01)

(52) U.S. Cl.
CPC ..... *G01N 27/44791* (2013.01); *C12Q 1/6825* (2013.01); *C12Q 1/6869* (2013.01); *C12Q 2565/607* (2013.01); *C12Q 2565/631* (2013.01)

(58) Field of Classification Search
None
See application file for complete search history.

(56) References Cited

U.S. PATENT DOCUMENTS 10,330,639 B2 6/2019 Keyser
10,983,091 B2 4/2021 Keyser

OTHER PUBLICATIONS

Hall et al., "Hybrid pore formation by directed insertion of a-haemolysin into solid-state nanopores," Nature Nanotechnology, 2010, vol. 5, Iss. 12, pp. 874-877. (Year: 2010).*
(Continued)

*Primary Examiner* — Matthew D Krcha
(74) *Attorney, Agent, or Firm* — Sheridan Ross P.C.

(57) ABSTRACT

A method is provided of controlling the functionality of a substrate containing at least one nanopore. The method includes the steps of: introducing to the substrate a solution containing a molecular construct having a body formation which defines an aperture and a tail formation extending from the body formation; applying a potential difference across the substrate to thread the tail formation through the nanopore thereby docking the molecular construct to the substrate with the aperture aligned with the nanopore such that the sleeve formation lines the nanopore; and expelling the molecular construct from the substrate by varying the potential difference. A DNA construct for docking to a substrate having a nanopore is also provided, the construct having a body formation which defines an aperture, and a tail formation extending from the body formation for threading through the nanopore to dock the construct to the substrate with the aperture and nanopore in alignment.

14 Claims, 9 Drawing Sheets

Figure 1:
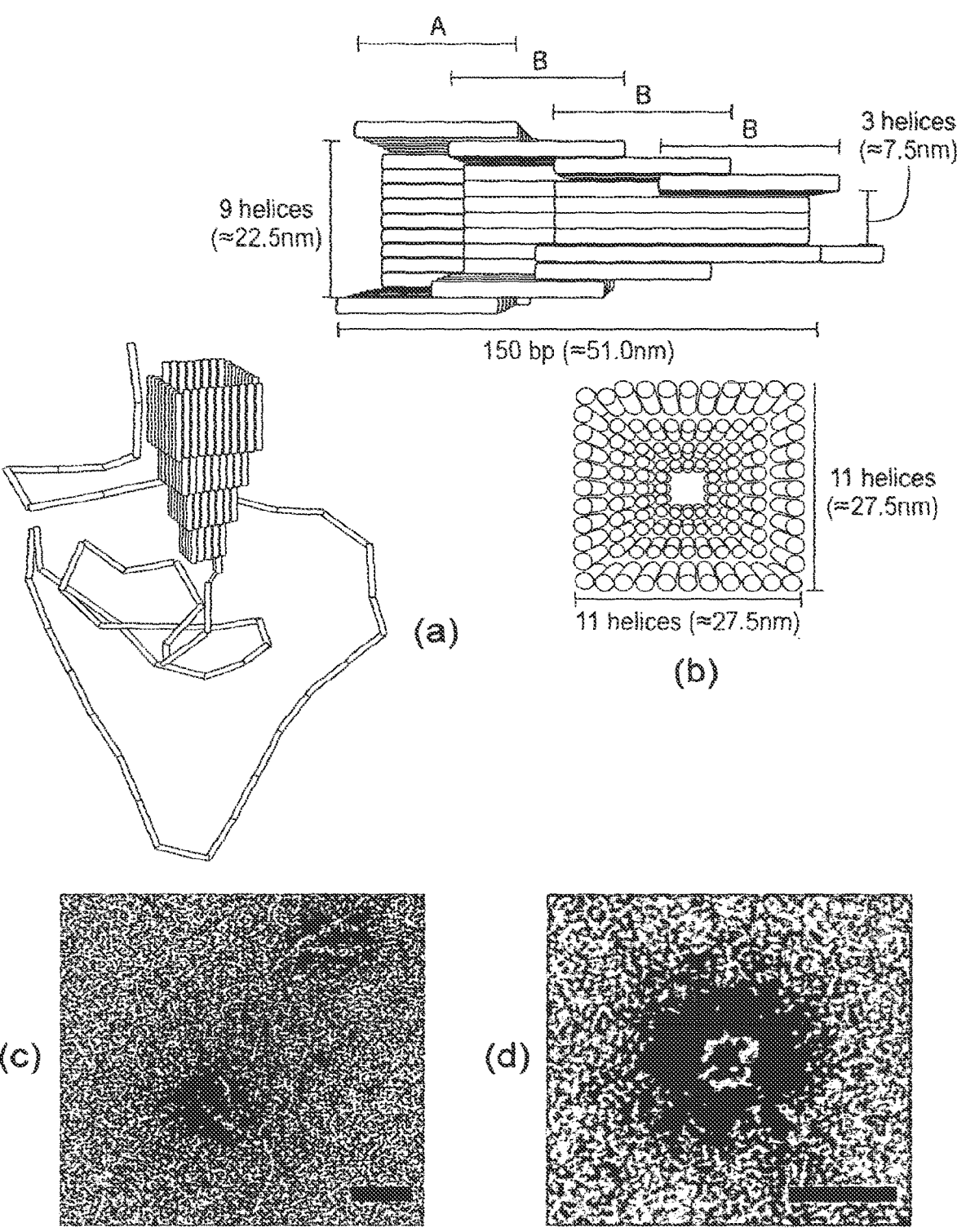

Related U.S. Application Data continuation of application No. 14/361,381, filed as application No. PCT/GB2012/053033 on Dec. 6, 2012, now Pat. No. 10,330,639.

(56) References Cited

OTHER PUBLICATIONS

Torring et al., "DNA origami: a quantum leap for self-assembly of complex structures," Chem Soc Rev, 2011, 40, pp. 5636-5646. (Year: 2011).*

International Search Report and Written Opinion for International (PCT) Patent Application No. PCT/GB2012/053033 mailed Feb. 7, 2013, 14 pages.

Akhshi et al., "Free-Energy Landscapes of Ion Movement through a G-Quadruplex DNA Channel," Angewandte Chemie International Edition, 2012, vol. 51, Iss. 12, pp. 2850-2854.

Bell et al., "DNA Origami Nanopores," Nano Letters, 2012, vol. 12, Iss. 1, pp. 512-517.

Bockelmann et al., "Unzipping DNA with Optical Tweezers: High Sequence Sensitivity and Force Flips," Biophysical Journal, vol. 82, Mar. 2002, pp. 1537-1553.

Branton et al., "The potential and challenges of nanopore sequencing," Nature Biotechnology, 2008, vol. 26, No. 10, pp. 1146-1153.

Clarke et al., "Continuous base identification for single-molecule nanopore DNA sequencing," Nature Nanotechnology, 2009, vol. 4, Iss. 4, pp. 265-270.

Dekker, "Solid-state nanopores," Nature Nanotechnology, 2007, vol. 2, Iss. 4, pp. 209-215.

Dietz et al., "Folding DNA into Twisted and Curved Nanoscale Shapes," Science, 2009, vol. 325, Iss. 5941, pp. 725-730.

Douglas et al., "Rapid prototyping of 3D DNA-origami shapes with caDNAno," Nucleic Acids Research, 2009, vol. 37, No. 15, pp. 5001-5006.

Douglas et al., "Self-assembly of DNA into nanoscale three-dimensional shapes" Nature, 2009, vol. 459, No. 7245, pp. 414-418.

Forman et al., "Toward Artificial Ion Channels: A Lipophilic G-Quadruplex," Journal of the American Chemical Society, 2000, vol. 122, Iss. 17, pp. 4060-4067.

Hall et al., "Hybrid pore formation by directed insertion of a-haemolysin into solid-state nanopores," Nature Nanotechnology, 2010, vol. 5, Iss. 12, pp. 874-877.

Han et al., "DNA Origami with Complex Curvatures in Three-Dimensional Space," Science, 2011, vol. 332, Iss. 6027, pp. 342-346.

Hernandez-Ainsa et al., "DNA Origami Nanopores for Controlling DNA Translocation," ACS Nano, vol. 7, No. 6, 2013 pp. 6024-6030.

Hernandez-Ainsa et al., "Voltage-Dependent Properties of DNA Origami Nanopores," Nano Letters, vol. 14, 2014, pp. 1270-1274.

Jahn et al., "Functional Patterning of DNA Origami by Parallel Enzymatic Modification," Bioconjugate Chemisty, 2011, vol. 22, Iss. 4, pp. 819-823.

Jungmann et al., "Single-Molecule Kinetics and Super-Resolution Microscopy by Fluorescence Imaging of Transient Binding on DNA Origami," Nano Letters, 2010, vol. 10, Iss. 11, pp. 4756-4761.

Kasianowicz et al., "Characterization of individual polynucleotide molecules using a membrane channel," Proceedings of the National Academy of Sciences of the United States of America, 1996, vol. 93, Iss. 24, pp. 13770-13773.

Kaucher et al., "A Unimolecular G-Quadruplex that Functions as a Synthetic Transmembrane Na+ Transporter," Journal of the American Chemical Society, 2006, vol. 128, Iss. 1, pp. 38-39.

Ke et al., "Multilayer DNA Origami Packed on a Square Lattice," Journal of the American Chemical Society, 2009, vol. 131, Iss. 43, pp. 15903-15908.

Keyser et al., "Controlling molecular transport through nanopores," Journal of the Royal Society Interface, 2011, vol. 8, Iss. 63, pp. 1369-1378.

Keyser et al., "Direct force measurements on DNA in a solid-state nanopore," Nature Physics, 2006, vol. 2 Iss. 7, pp. 473-477.

Keyser et al., "Optical tweezers for force measurements on DNA in nanopores," Review Of Scientific Instruments, 2006, vol. 77, Iss. 10, pp. 105105-1-105105-9.

Langecker et al., "Synthetic Lipid Membrane Channels Formed by Designed DNA Nanostructures," Science, 2012, vol. 338, Iss. 6109, pp. 932-936.

Li et al., "DNA molecules and configurations in a solid-state nanopore microscope," Nature Materials, 2003, vol. 2, Iss. 9, pp. 611-615.

Li et al., "Ion-beam sculpting at nanometre length scales," Nature, 2001, vol. 412, No. 6843, pp. 166-169.

Liedl et lal., "Self-assembly of three-dimensional prestressed tensegrity structures from DNA," Nature Nanotechnology, 2010, vol. 5, Iss. 7, pp. 520-524.

Mathe et al., "Nanopore Unzipping of Individual DNA Hairpin Molecules," Biophysical Journal, vol. 87, Nov. 2004, pp. 3205-3212.

McNally et al., "Optical Recognition of Converted DNA Nucleotides for Single-Molecule DNA Sequencing Using Nanopore Arrays," Nano Letters, 2010, vol. 10, Iss. 6, pp. 2237-2244.

Pal et al., "Site-Specific Synthesis and In Situ Immobilization of Fluorescent Silver Nanoclusters on DNA Nanoscaffolds by Use of the Tollens Reaction," Angewandte Chemie International Edition, 2011, vol. 50, Iss. 18, pp. 4176-4179.

Peng et al., "Reverse DNA translocation through a solid-state nanopore by magnetic tweezers," Nanotechnology, 2009, vol. 20, No. 18, 185101, 8 pages.

Plesa et al., "Velocity of DNA during Translocation through a Solid-State Nanopore," Nano Letters, vol. 15, 2015, pp. 732-737.

Rothemund, "Folding DNA to create nanoscale shapes and patterns," Nature, 2006, vol. 440, No. 7082, pp. 297-302.

Sauer-Budge et al., "Unzipping Kinetics of Double-Stranded DNA in a Nanopore," Physical Review Letters, vol. 90, No. 23, Jun. 13, 2003, 4 pages.

Seeman, "Nanomaterials Based on DNA," Annual Review of Biochemistry, 2010, vol. 79, pp. 65-87.

Siwy et al., "Rectification and voltage gating of ion currents in a nanofabricated pore," Europhysics Letters, 2002, vol. 60, Iss. 3, pp. 349-355.

Siwy, "Ion-Current Rectification in Nanopores and Nanotubes with Broken Symmetry," Advanced Functional Materials, 2006, vol. 16, Iss. 6, pp. 735-746.

Smeets et al., "Salt Dependence of Ion Transport and DNA Translocation through Solid-State Nanopores, " Nano Letters, 2006, vol. 6, No. 1, pp. 89-95.

Stein et al., "Single-Molecule FRET Ruler Based on Rigid DNA Origami Blocks," ChemPhysChem (A European Journal of Chemical Physics and Physical Chemistry), 2011, vol. 12, Iss. 3, pp. 689-695.

Steinbock et al., "Detecting DNA Folding with Nanocapillaries," Nano Letters, 2010, vol. 10, Iss. 7, pp. 2493-2497.

Steinbock et al., "Probing DNA with micro- and nanocapillaries and optical tweezers," Journal Of Physics: Condensed Matter, 2010, vol. 22, No. 45, 454113, 8 pages.

Steinbock et al., "Sensing DNA-coatings of microparticles using micropipettes," Biosensors and Bioelectronics, 2009, vol. 24, Iss. 8, pp. 2423-2427.

Storm et al., "Fabrication of solid-state nanopores with single-nanometre precision," Nature Materials, 2003, vol. 2, Iss. 8 pp. 537-540.

Subramanian et al., "The Label-Free Unambiguous Detection and Symbolic Display of Single Nucleotide Polymorphisms on DNA Origami," Nano Letters, 2011, vol. 11, Iss. 2, pp. 910-913.

Thorsen et al., "Microfluidic Large-Scale Integration," Science, 2002, vol. 298, No. 5593, pp. 580-584.

Torring et al., "DNA Origami: A Quantum Leap for Self-Assembly of Complex Structures," Chemical Society Reviews, vol. 40, No. 12, Dec. 2011, pp. 5636-5646.

Voigt et al., "Single-molecule chemical reactions on DNA origami," Nature Nanotechnology, 2010, vol. 5, Iss. 3, pp. 200-2003.

Wanunu et al., "Chemically Modified Solid-State Nanopores," Nano Letters, 2007, vol. 7, No. 6, pp. 1580-1585.

(56)  References Cited

OTHER PUBLICATIONS

Wei et al., "DNA Origami Gatekeepers for Solid-State Nanopores," Angewandte Chemie International Edition, 2012, vol. 51, Iss. 20, pp. 4864-4867.

Yusko et al., "Controlling protein translocation through nanopores with bio-inspired fluid walls," Nature Nanotechnology, 2011, vol. 6, Iss. 4, pp. 253-260.

Official Action for U.S. Appl. No. 14/361,381, mailed Jun. 8, 2016, 8 pages. Restriction Requirement.

Official Action for U.S. Appl. No. 14/361,381, mailed Jul. 25, 2016, 4 pages.

Official Action for U.S. Appl. No. 14/361,381, mailed Nov. 17, 2016, 8 pages.

Official Action for U.S. Appl. No. 14/361,381, mailed Jun. 1, 2017, 9 pages.

Official Action for U.S. Appl. No. 14/361,381, mailed Aug. 31, 2018, pages.

Notice of Allowance for U.S. Appl. No. 14/361,381, dated Feb. 13, 2019, 8 pages.

Notice of Allowance for U.S. Appl. No. 16/404,164, dated Dec. 21, 2020, 8 pages.

* cited by examiner (a)

(b)

(a)

(b)

(c)

(d)

(a)

(b)

NANOPORE FUNCTIONALITY CONTROL

CROSS REFERENCE TO RELATED APPLICATIONS

This application is a continuation application of U.S. patent application Ser. No. 16/404,164, filed May 6, 2019, which is continuation application of U.S. patent application Ser. No. 14/361,381, filed May 29, 2014, now U.S. Pat. No. 10,330,639, which is a national stage application under 35 U.S.C. 371 and claims the benefit of PCT Application No. PCT/GB2012/053033 having an international filing date of Dec. 6, 2012, which designated the United States, which PCT application claimed the benefit of Great Britain Application No. 1120910.3 filed Dec. 6, 2011, the disclosure of both the above-identified applications are incorporated herein by reference.

The present invention relates to a method of controlling the functionality of a substrate containing at least one nanopore and a DNA construct for insertion into a nanopore.

Single nanopores in insulating barriers are under investigation as sensors for single molecules in solution[1]. Since the first experiments on DNA and RNA translocations by Kasianowicz et al.[2] research activities in nanopore sensing have grown rapidly. Single solid-state nanopores produced by silicon nanotechnology and ion beam milling were first employed for ionic current-based detection of DNA by Li et al.[3]. DNA folding detection with nanocapillaries[4], the development of alternative fabrication protocols like transmission-electron drilling of solid-state nanopores[5], or the combination of nanopores with other single-molecule techniques like optical tweezers[6], magnetic tweezers[7] or single molecule fluorescence[8] has given the field new impetus.

In a typical application, the nanopore separates two chambers containing an aqueous solution of positive and negative salt ions. Additionally, one of the reservoirs contains a molecule of interest. When a potential difference is applied across the membrane an ionic current can be measured as ions pass through the nanopore. Molecules translocating through the nanopore transiently block the current. The change in current and dwell time as the molecule passes through the nanopore can be measured with a sensitive current detector. The current traces recorded can then be analysed to infer molecular properties.

Two remaining challenges are the control of the exact shape of nanopores and the analyte-specific modification of their cavities. Coating with lipid bilayers[9] or polymersl[10] provides means of modifying the surface properties of solid-state nanopores, but the creation of fixed structures with nanometer scale control of geometry and positioning of functional chemical motifs has yet to be demonstrated. The recent combination of hybrid biological and solid-state nanopores[11] crossed the boundary between nanopores extracted from living organisms and those derived from silicon nanotechnology. While this achievement allows for the design of nanopores adapted for molecular sensing[12] and sequencing[13], protein nanopores have fixed diameters which are often in the single nanometer range. This currently limits the range of analytes to unfolded proteins or single-stranded DNA chains.

It would be desirable to have a method for forming easily tunable nanopores with diameters from 1 nm to 100 nm that could therefore be applied to a much wider range of analytes. Further, as solid-state nanopores can be high cost items which may be problematic to manufacture reproducibly (particularly when the nanopores have diameters of 20 nm or less), it would be desirable to improve the usable life and/or reusability of such nanopores. The present invention is at least partly based on a realisation that control of nanopore size and functionality in a hybrid nanopore can be achieved by the application of a potential difference.

Accordingly, in a first aspect, the present invention provides a method of controlling the functionality of a substrate containing at least one nanopore, the method including the steps of:

introducing to the substrate a solution containing a molecular construct having a body formation which defines an aperture and a tail formation extending from the body formation;

applying a potential difference across the substrate to thread the tail formation through the nanopore thereby docking the molecular construct to the substrate with the aperture aligned with the nanopore; and expelling the molecular construct from the substrate by varying the potential difference.

Thus, advantageously, the molecular construct can be used to control the functionality of the nanopore (e.g. by controlling the construct's size, geometry, chemical functionality, etc. particularly at the aperture), but the construct can be removed, allowing the substrate e.g. to be re-used for a different analyte.

The method of the first aspect may have any one or, to the extent that they are compatible, any combination of the following optional features.

The variation of the potential difference may typically include a reversal of the potential across the substrate.

The method may include a further step of flushing the expelled molecular construct away from the substrate after its expulsion, for example by the use of an appropriate micro-fluidics arrangement. Indeed, such an arrangement can also be used to introduce the solution containing the molecular construct to the substrate in the first place.

The method may include further steps after the expelling step of: introducing to the substrate a solution containing a different molecular construct having a body formation which defines an aperture and a tail formation extending from the body formation; and re-applying a potential difference across the substrate to thread the tail formation through the nanopore thereby docking the different molecular construct to the substrate with the aperture aligned with the nanopore. In this way, the functionality of the nanopore can be controllably and repeatably modified. For example, a range of different molecular constructs can be successively docked to the substrate to make the nanopore functionally sensitive to a corresponding range of different analytes.

In a second aspect, the present invention provides a method of detecting the presence of an analyte in a solution, the method including the steps of:

(a) providing a substrate containing at least one nanopore;

(b) introducing to the substrate a solution which may contain the analyte, and a molecular construct having a body formation which defines an aperture, and which has a one or more binding sites for the analyte at the aperture;

(c) applying a potential difference across the substrate to dock the molecular construct to the substrate with the aperture aligned with the nanopore, and measuring the corresponding change in ionic current through the nanopore;

(d) comparing the measured change in ionic current to a reference change in ionic current; and

(e) determining that the analyte is present in the solution when the measured change in ionic current differs from the reference change in ionic current by more than a predetermined amount.

Thus the analyte, when present, binds to the molecular construct in the solution and, because the one or more binding sites are at the aperture, can thereby fully or partially block the aperture. When the molecular construct docks to the substrate, the blockage affects the ability of ions to pass through the nanopore and hence affects the measured change in ionic current.

Advantageously, analyte specificity can thereby be provided by the molecular construct. Thus if a further solution contains a molecule which is of similar size to the analyte but which does not bind to the molecular construct, applying steps (b) to (e) to both solutions should allow a user to distinguish between the solution containing the analyte and the further solution.

The method of the second aspect may have any one or, to the extent that they are compatible, any combination of the following optional features.

The applying step (c) may include repeatedly performing the sub-steps of:

(i) applying the potential difference across the substrate to dock the molecular construct to the substrate with the aperture aligned with the nanopore, and measuring the corresponding change in ionic current through the nanopore; and (ii) expelling the molecular construct from the substrate by varying (e.g. reversing) the potential difference; and wherein, in the comparing step (d), the measured change in ionic current is an average measured change derived from the repeated measurements of sub-step (c-i). Repeating the measurements can help to improve detection accuracy.

Typically, the measured change and the reference change are decreases in ionic current.

The reference change can conveniently be the change in ionic current that would have occurred if there had been no analyte in the solution. Indeed, the method may further include the steps of:

(A) providing a substrate containing at least one nanopore;

(B) introducing to the substrate a solution containing the molecular construct in the absence of the analyte; and (C) applying a potential difference across the substrate to dock the molecular construct, in the absence of the analyte, to the substrate with the aperture aligned with the nanopore, and measuring the corresponding change in ionic current through the nanopore; and wherein, in the comparing step (d), the reference change in ionic current is the change in current measured at step (C). The solution of step (B) preferably has the same ionic strength and pH as the solution of step (b). For example, it may contain an identical concentration of the same dissolved salt and be identically buffered.

The applying step (C) may include repeatedly performing the sub-steps of:

(i) applying the potential difference across the substrate to dock the molecular construct, in the absence of the analyte, to the substrate with the aperture aligned with the nanopore, and measuring the corresponding change in ionic current through the nanopore; and (ii) expelling the molecular construct from the substrate by varying (e.g. reversing) the potential difference; and wherein, in the comparing step (d), the reference change in ionic current is an average measured change derived from the repeated measurements of sub-step (C-i).

The substrate of step (A) can be a different but equivalent substrate to the substrate of step (a). Steps (A) to (C) can then be performed before, during or after the performance of steps (a) to (c).

Another option, however, is for the substrate of step (A) to be the same substrate as the substrate of step (a). Steps (B) to (C) can then be performed before or after the performance of steps (b) to (c). However, whichever is performed first, the method may include a further step of flushing the first solution away from the substrate after expulsion of that solution's molecular construct, and before the introduction of the second solution. Again, the flushing can be performed by the use of an appropriate micro-fluidics arrangement. The arrangement can also be used to introduce the first and second solutions to the substrate.

The analyte may be an antibody.

The molecular construct may further have a tail formation extending from the body formation, the tail formation being threaded through the nanopore to dock the molecular construct to the substrate when the potential difference is applied across the substrate.

The method of the first or second aspect may have any one or, to the extent that they are compatible, any combination of the following optional features.

The substrate may have plural nanopores, and the apertures of respective molecular constructs may be aligned with the nanopores by the application of the potential difference across the substrate. Likewise, the plural molecular constructs may be expelled from the substrate by varying the potential difference.

The substrate may be a silicon-nitride or silicon-oxide substrate, e.g. with one or more electron or ion beam drilled nanopores.

Preferably, the body formation has a docking surface which contacts the substrate when the construct is docked thereto, at least the docking surface being hydrophilic. In a typically aqueous solution, this can help to prevent the body formation from binding too tightly to a mating surface of the substrate, whereby variation of the potential difference can more easily expel the molecular construct from the substrate. In contrast, the α-hemolysin protein pore disclosed by Hall et al.[11] is hydrophobic.

Preferably, the body formation can include or be a sleeve formation which defines the aperture, the application of the potential difference causing the molecular construct to dock to the substrate such that the sleeve formation lines the nanopore. The above-mentioned docking surface can include or be the external surface of the sleeve formation.

Preferably, the molecular construct is a DNA construct. Advantageously, DNA is hydrophilic, which, as discussed above, promotes the exchangeability of the construct. Further, the DNA construct can conveniently be made by DNA-based self-assembly or "origami" techniques. DNA-based self-assembly[14] employs the programmability of DNA sequences to build rationally designed objects of ever increasing complexity. Owing to the development of DNA origami[15] it is now possible to design and fabricate almost arbitrary nanosized shapes[16]. The origami method typically uses a 7-8 kb long ml3mp18-based single-strand as a scaffold for the assembly of hundreds of distinct synthetic staple strands. Each of these staples can potentially be extended with a nucleotide (nt) sequence of interest or a wide range of chemical modifications[17]. In addition, the use of DNA origami allows for the addition of functional chemical groups, fluorophores, gold nanoparticles etc. at sub-nanometre position accuracy by employing modifications to the oligonucleotide staple strands used to fold the long DNA single strand[25]. These modifications have the potential for the integration of DNA origami and nanopores with techniques such as fluorescence detection and Raman spectroscopy. Thus DNA is well suited for the synthesis of programmable constructs with chemically adjustable cavities and custom tailored geometries.

Indeed, in a third aspect, the present invention provides a DNA construct (e.g. a DNA origami construct) for docking to a substrate having a nanopore, the construct having a body formation which defines an aperture, and a tail formation extending from the body formation for threading through the nanopore to dock the construct to the substrate with the aperture and nanopore in alignment. The body formation can include or be a sleeve formation which defines the aperture and which lines the nanopore when the construct is docked to the substrate. The construct can include functional chemical groups, fluorophores, and/or gold nanoparticles.

Further, in a fourth aspect, the present invention provides the use of DNA origami to form the DNA construct of the second aspect.

Further optional features of the invention will now be set out. These are applicable singly or in any combination with any of the above aspects of the invention.

The nanopore preferably has a diameter of 100 nm or less, and more preferably of 50 or 20 nm or less. Nanopores of 20 nm diameter or less are generally particularly difficult to produce reproducibly, or indeed at all. Thus the use of the molecular construct in relation to the nanopores of this size can be particularly beneficial, allowing the same nanopore to be used for repeatedly, e.g. for different analytes. This not only helps to relieve the burden of producing numbers of nanopores in the first place, but allows the same nanopore to be used for comparative testing.

The nanopore preferably has a diameter of 1 nm or more, and more preferably of 2 or 5 nm or more.

Further optional features of the invention are set out below.

Embodiments of the invention will now be described by way of example with reference to the accompanying drawings in which:

FIG. 1: DNA origami design. (a) Schematic representation of the DNA origami structure with the double stranded overhang. Double helices are presented as rods. (b) Top: Side view of the nanopore section of the DNA origami structure with helices shown as cylinders. The overall length of the nanopore is 150 bp (51.0 nm) with the smallest opening of 7.5×7.5 $nm^2$. Length A=40 bp (13.6 nm), length B=48 bp (16.3 nm). Bottom: Top view of the structure, indicating the square shape with 11 by 11 helices with a total area of 27.5×27.5 $nm^2$. (c) Transmission electron microscope (TEM) images of assembled DNA origami constructs negatively stained with uranyl acetate. (d) TEM image of upright standing DNA origami construct, cf. bottom view of (b). Scale bars=40 nm.

Figure 2:
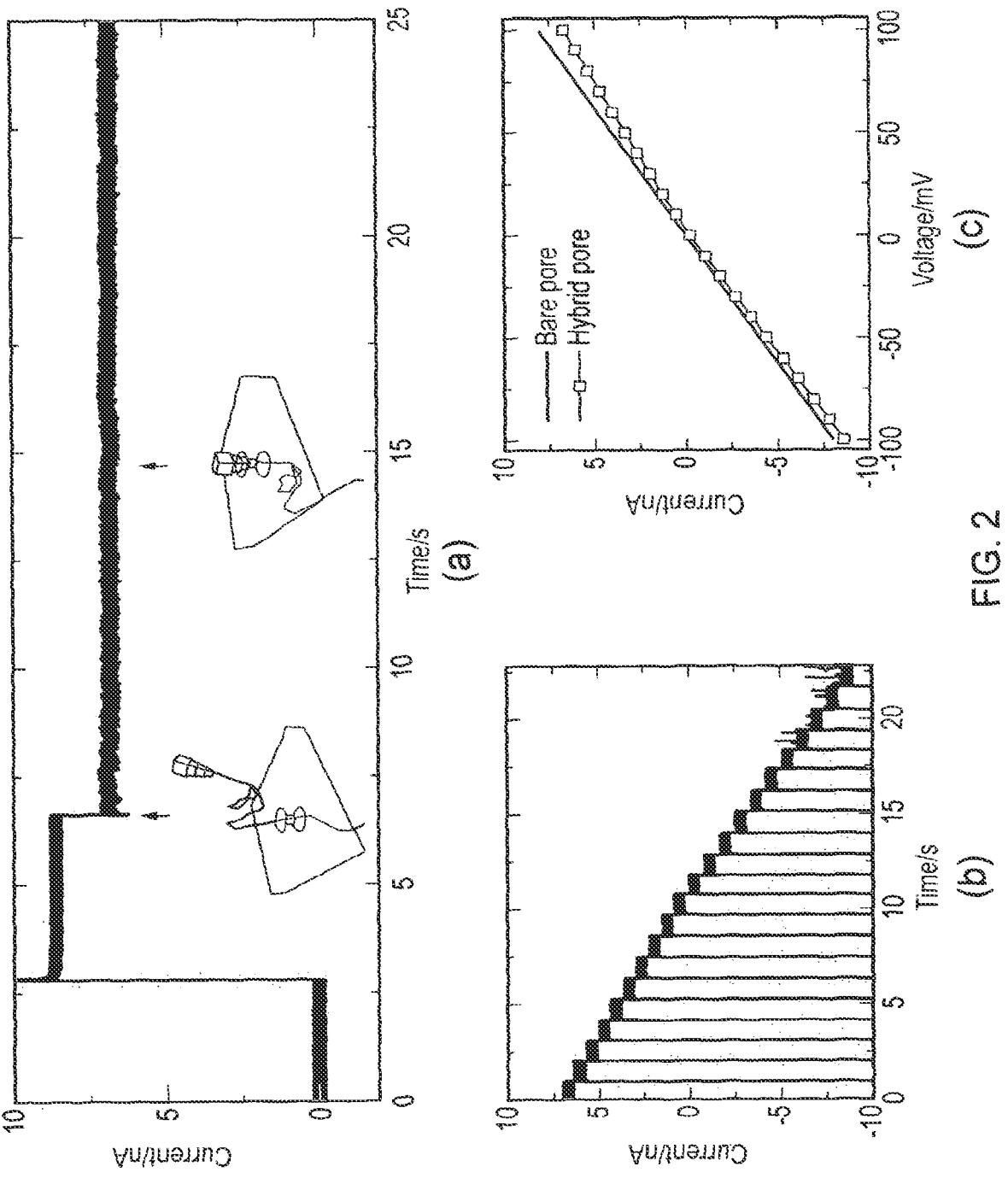

FIG. 2: Characterization of a single hybrid nanopore. (a) Current as a function of time through a single solid-state nanopore with a diameter of 13 nm. Voltage is switched from 0 mV to +100 mV at 2.8 s. At 6.2 s a sudden drop in current indicates insertion of a DNA origami construct, see arrow. (b) Current as a function of time through a single hybrid nanopore while reducing the voltage in 10 mV steps. (c) Current-voltage characteristic of the hybrid nanopore (line/dots) in comparison with the current-voltage characteristic of the bare solid-state nanopore (plain line).

Figure 3:
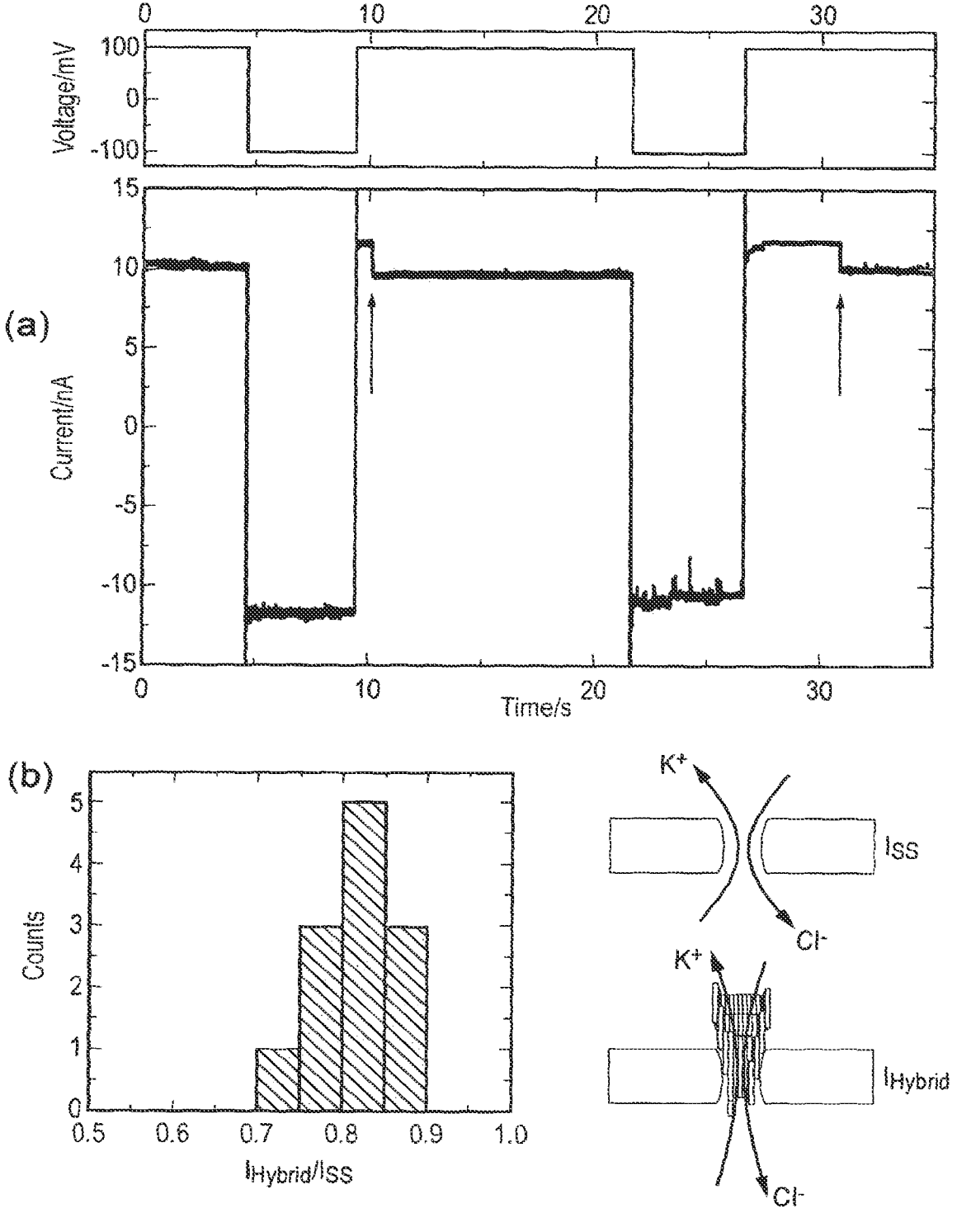

FIG. 3: Repeated insertion of DNA origami constructs into an 18 nm diameter solid-state nanopore. (a) Top panel: applied voltage as a function of time for insertion of DNA origami constructs. At +100 mV hybrid nanopores are stable while at −100 mV the DNA origami construct can be driven out of the solid-state nanopore. Lower panel: corresponding ionic current trace showing formation of hybrid nanopores, indicated by the arrows. (b) Histogram of the relative current change for 12 insertions, measured in 5 different experiments and nanopores. The relative current change is the quotient of the hybrid pore current $I_{Hybrid}$ divided by the open pore current $I_{SS}$. Right: Sketches of the situations with $I_{SS}$ and $I_{Hybrid}$.

Figure 4:
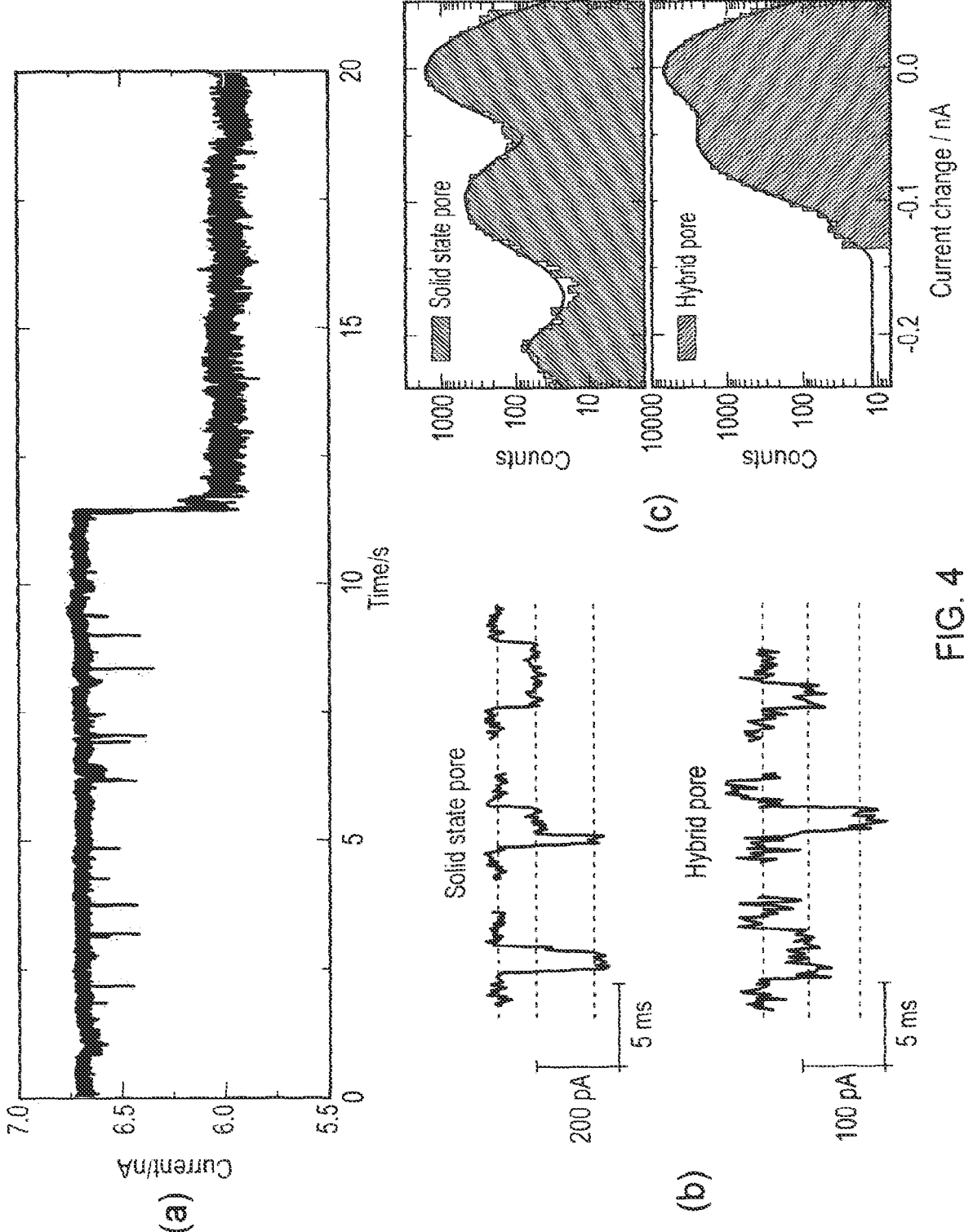

FIG. 4: λ-DNA events through bare solid-state nanopore and hybrid nanopores. (a) Ionic current as a function of time at +100 mV for an experiment with both DNA origami and λ-DNA in the solution, with 0.5 nM and 1.0 nM concentration respectively. For t<11.4 s, DNA translocations through the bare nanopore (15 nm diameter) are observed. After formation of the hybrid nanopore, events for the hybrid nanopore are observed. (b) Typical events for the bare nanopore shown top and the hybrid nanopore shown bottom. (c) Current histograms indicating DNA translocations for the bare solid-state and hybrid nanopores. The baseline for both histograms was subtracted for easy comparison, and the current was digitally filtered at 3 kHz for clarity.

Figure 5:
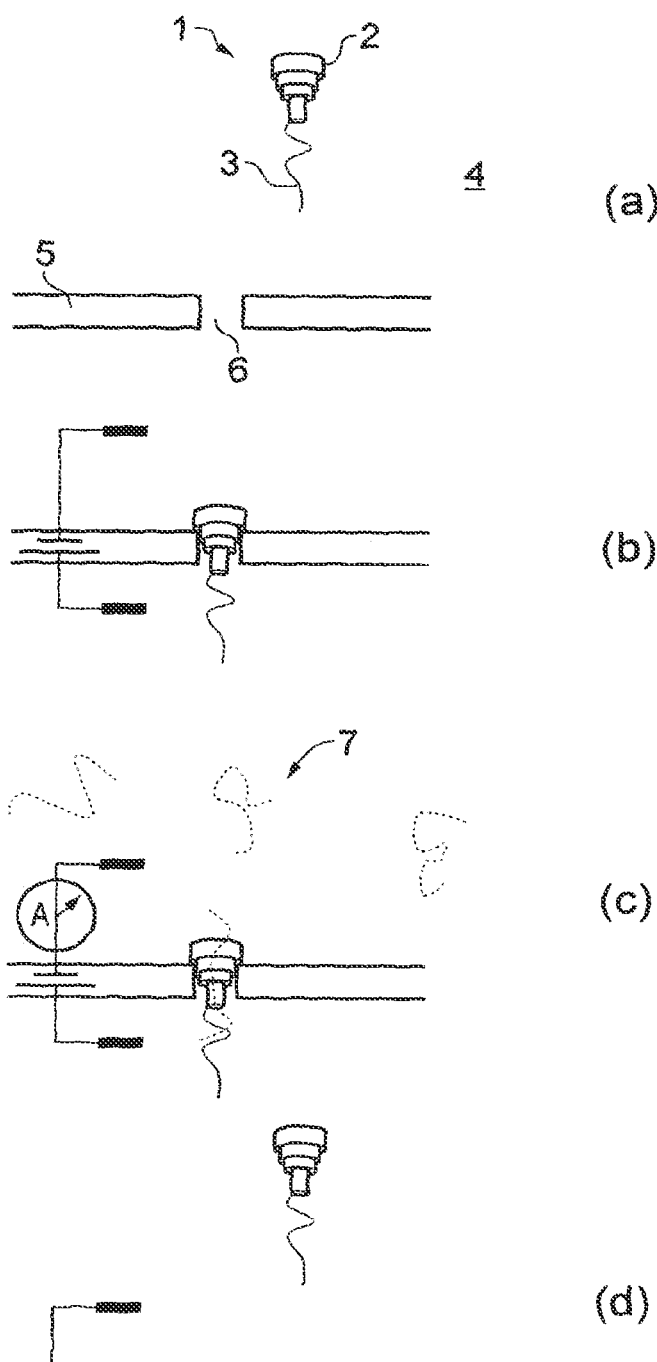

FIG. 5: a schematic representation of a complete testing cycle including: (a) the introduction of a DNA construct having a sleeve formation and tail formation into a reservoir on one side of a substrate having a nanopore; (b) application of a positive polarity potential difference to thread the tail formation through the nanopore and seat the sleeve formation in the nanopore; (c) testing of the current signature through the resulting hybrid nanopore when an analyte is introduced into the reservoir; and (d) expulsion of the construct on application of a negative polarity potential difference in readiness e.g. for the introduction of a different DNA construct into the reservoir and a further testing cycle.

Figure 6:
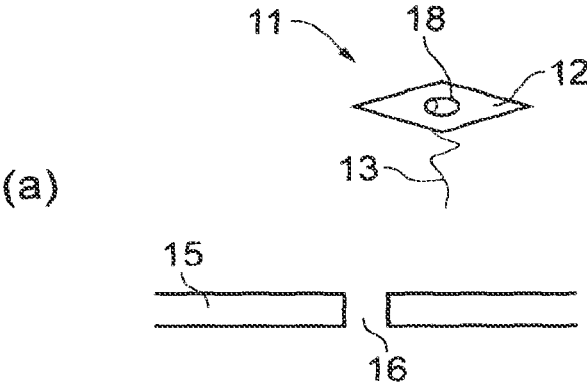
Figure 6:
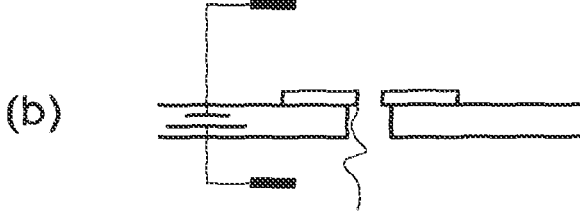

FIG. 6: a schematic representation of: (a) the introduction of a DNA construct to a substrate having a nanopore, the construct having a body formation in the form of a plate defining a central aperture, with a tail formation extending from an edge of the aperture; and (b) the docking of the construct to the substrate, with the tail formation threaded through the aperture, the flat body formation overlaying the substrate, and the central aperture aligned with the nanopore.

Figure 7:
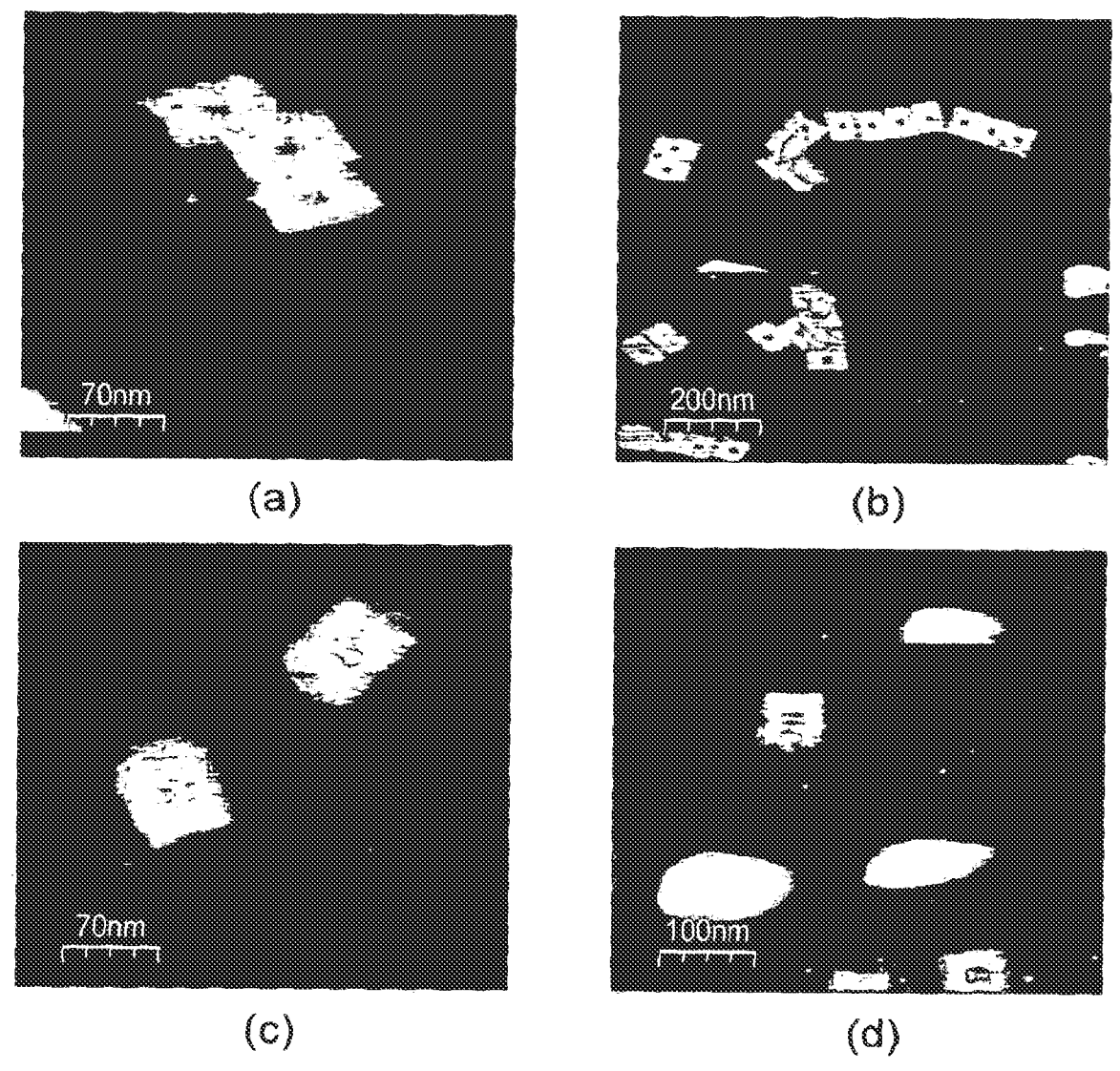

FIG. 7: atomic force microscopy pictures of DNA constructs docked to a substrate (a) and (b) without streptavidin bound to the constructs, and (c) and (d) with streptavidin bound to the constructs.

Figure 8:
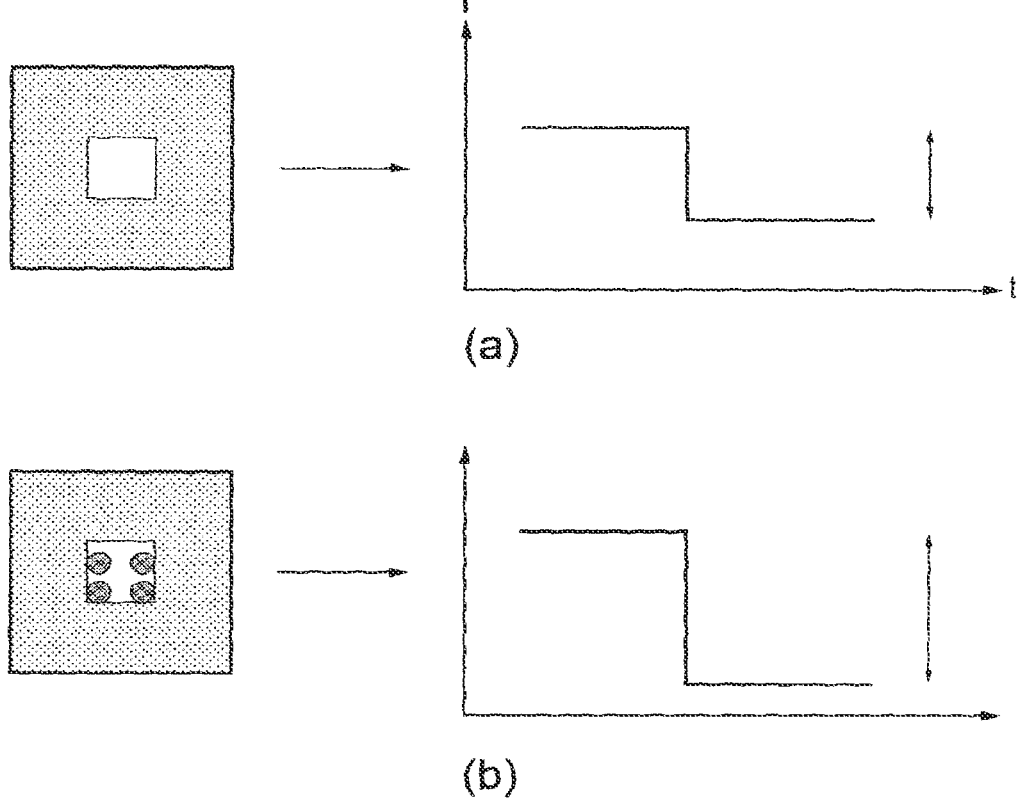

FIG. 8: schematic plots of the change in ionic current expected on docking the constructs of FIG. 7 (a) from a solution without streptavidin and (b) from a solution with streptavidin.

Figure 9:
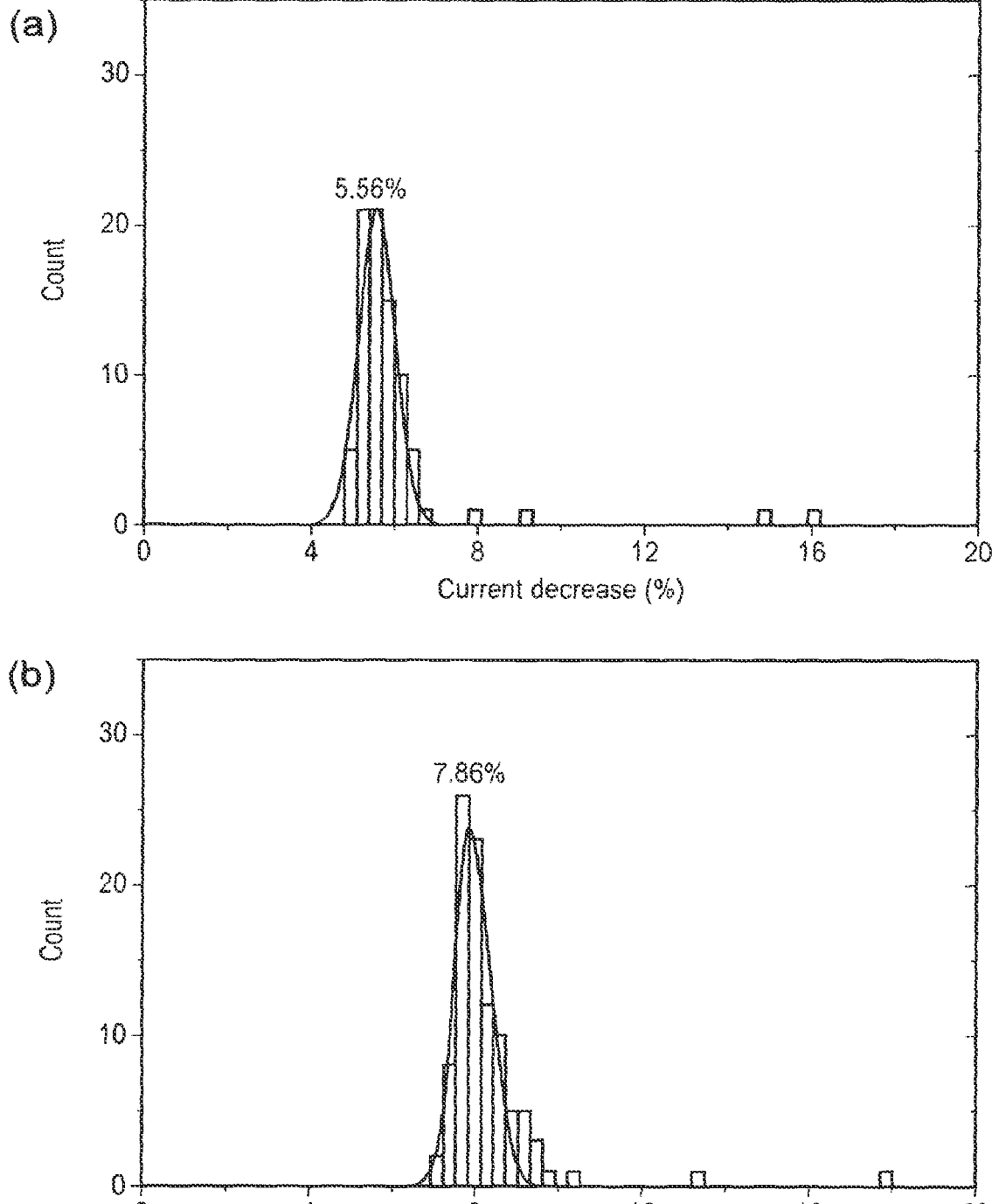

FIG. 9: histograms of actual percentage current decrease for repeated docking experiments using the constructs of FIG. 7 (a) from a solution without streptavidin and (b) from a solution with streptavidin.

In the following we demonstrate the successful insertion of DNA constructs into solid-state nanopores. Further, we demonstrate that such constructs can be controllably and repeatedly inserted into the nanopores and can be used for resistive-pulse sensing. Finally, we describe a technique for detecting specific analytes.

Materials and Methods

A DNA origami construct was designed using the square-lattice version of the caDNAno software from Douglas et al.[18]. As the scaffold strand, the 8634 nt-long m13mp18-based[16a] single strand was chosen and cut at the EcoRI and BamHI restriction sites. Of the 8613 bases of the cut scaffold, 6264 were incorporated into an origami structure with the help of 142 staple strands and 2349 bases were allowed to form a linear extension of one of the helices. This part of the single-stranded scaffold was complemented with 49 consecutive 40 mers and 48 mers to form a 2344 basepairs (bp) long double strand with 48 nicks which acted as a leash to ensure correctly-oriented trapping of the DNA construct into the solid-state nanopore.

The constructs were assembled by heating a Tris-HCl (10 mM)–EDTA (1 mM) buffer (pH 8.0) containing the cut scaffold (10 nM), the staple strands and the complements of the leash (100 nM each), and 14 mM $MgCl_2$. The assembled structures were purified from the excess staple strands by either agarose gel electrophoresis or centrifugation with 100 kDa MWCO filters.

Nanopores with diameters between 12-18 nm were fabricated in silicon-nitride (SiN) membranes with an FEI Tecnai F20 transmission electron microscope (TEM) equipped with a field emission gun (FEG) which was operated at an acceleration voltage of 200 kV and an extraction voltage of 4000V. The SiN membranes were 30 nm thick with 50×50 $\mu m^2$ windows (DuraSin, Protochips, USA).

The SiN chip containing a nanopore was sealed into polydimethylsiloxane (PDMS) microfluidic channels. The PDMS (Sylgard 184, Dow Corning) was made by mixing base and curing agent in a weight ratio of 10:1 and curing in an aluminum mold for 10 minutes at 150° C. The aluminum mold design comprised channels at either side of the pore for introducing buffer and a required sample volume of only 10 μL. The PDMS was plasma-bonded to a glass slide to prevent leaks[19]. Before introducing buffer, the nanopore containing TEM chip was plasma cleaned for 1 minute. A Gigaohm seal was then formed between the two reservoirs of the PDMS by painting fresh PDMS around the edge of the chip and curing on a hot plate for 60 seconds at 120° C. Subsequently, buffer solution was added to both sides of the chip.

For ionic current measurements, Ag/AgCl electrodes were fabricated by electro-deposition of a AgCl layer onto 0.2 μm thick silver wire. The two electrodes were placed in the reservoirs on either side of the nanopore and connected to the headstage of an Axopatch 200B amplifier (Molecular Devices, USA). The amplifier headstage and nanopore device were enclosed in a Faraday cage to reduce electromagnetic interference. All ionic current recordings were performed with the internal Bessel filter of the amplifier at 10 kHz and recorded at up to 100 kHz bandwidth. The data was later filtered for analysis. Voltages were set and currents recorded by custom written LabView software[4,20] or with ClampEx (Molecular Devices, USA).

For translocation experiments we used linearized λ-DNA (New England Biolabs, USA) diluted in the measurement buffer prior to all experiments. After purification DNA origami constructs were diluted to a concentration of approximately 0.5 nM in the measurement buffer.

DNA Origami Construct

An aim of the design process was to find an accessible geometry that would fit into the conical form of the solid-state nanopore while allowing for stable insertion in a wide range of nanopore diameters. A schematic overview of the construct is shown in FIG. 1. All lengths are calculated by assuming 0.34 nm helical step size per bp and an average center-to-center distance of 2.5 nm per helix pair (see FIG. 1b)[15, 21].

The geometry has a sleeve formation of staggered double helices whose z-axes are pointing into the solid-state pore forming four overlapping skirts with a quadratic base, the helices defining a central aperture. The innermost skirt is formed by 16 helices, 48 bp long (16.3 nm), where each face of this square cylinder is comprised of five parallel helices resulting in an outer edge length of 12.5 nm and an inner edge length of 7.5 nm, see FIG. 1b. The next skirt is built up from 24 helices (7 helices per face) and overlaps with the innermost skirt over a length of at least 16 bp to a maximum of 40 bp. The third layer consists of 32 helices and the outermost layer of 40 helices with each layer overlapping over at least 8 bp to a maximum of 16 bp. For the edge facing the solution (distal) we calculated a length of 11×2.5 nm=27.5 nm which is large enough to prevent slipping of the assembled structure into the solid-state pore, which in our experiments has a diameter of typically about 12-18 nm. In order to guide the voltage-driven self-assembly, we added a double stranded DNA tail to the tip of the sleeve formation. It is believed that the tail threads through the nanopore to assist and precede the insertion of the sleeve formation therein. The overall length of the origami structure without the tail is 51.0 nm, the outer diagonal diameter is 38.9 nm, while the centre opening is 7.5×7.5 $nm^2$. Typical TEM images recorded at 100 kV (JEM-1011, JEOL) of the correctly folded structure are shown in FIG. 1c and 1d, as side and top view, respectively. The segmented double stranded DNA tail can be observed in both images.

Hybrid Nanopore Formation

After a solid-state nanopore was assembled into a microfluidic measurement cell, the current-voltage characteristic was first tested in a 20 nm filtered buffer solution of 0.5×TBE, 5.5 mM $MgCl_2$, 1M KCl. FIG. 2 shows an example trace of the characteristic current signature observed after adding the DNA origami construct to one side of the solid-state nanopore. Recording in this experiment started at 0 mV and after 2.8 s+100 mV was applied (with positive polarity making the DNA construct move towards the solid-state nanopore). An initial ionic current of 8.7 nA was measured through the bare solid-state nanopore. After about 6.6 s we see a sudden drop in the ionic current indicating the correct insertion of a DNA origami construct into the solid-state nanopore. The newly formed hybrid nanopore was then tested by recording a current-voltage characteristic shown in FIG. 2b. The voltage was decreased from +100 to −100 mV in steps of −10 mV. The points shown in FIG. 2c are extracted by averaging over each current step. The line for the current-voltage characteristic of the bare solid-state nanopore was measured before adding the DNA origami solution. We observe that at positive voltages the current through the hybrid nanopore is lower than for the bare solid-state nanopore. The bare solid-state nanopore shows a linear IV curve whereas after the formation of a hybrid nanopore the IV curve shows rectification. This behavior is due to the asymmetry and the highly charged DNA surface of the hybrid nanopore[22], and is an important indication that the DNA origami structure is correctly assembled into the solid-state nanopore.

Repeated Construct Insertions

Our DNA origami constructs can be ejected from the solid-state nanopore by sudden reversal of the applied potential. This is an important feature allowing for error correction if a pore did not insert correctly or for exchanging different pores within the same experiment. The top part of FIG. 3a shows the applied voltage as a function of time switching between +100 and −100 mV. The corresponding ionic current trace is shown in the lower part of FIG. 3a. Initially, at +100 mV, a hybrid nanopore is present and a current of 10.2 nA is observed. Upon switching the voltage to −100 mV the current changes to −11.8 nA, but switching back to +100 mV leads to an increase of the current to +11.6 nA indicating the original open pore current and the disassembly of the hybrid nanopore. At this voltage the same or another construct is quickly inserted into the solid-state nanopore at 11.0 s (see arrow in FIG. 3a). The current stabilizes at approximately the same level as for the previous hybrid nanopore. At t=21.6 s the voltage is switched again to −100 mV to eject the origami structure. Upon switching back to +100 mV at 26.6 s the ionic current returns quickly to the open nanopore current only to fall back to the hybrid nanopore current of 10.0 nA at 31.0 s, indicating another successful assembly.

The histogram in FIG. 3b shows the relative current change defined as the hybrid nanopore current divided by the solid-state nanopore current at +100 mV for 12 insertions taken for 5 different nanopores. Insertion of the origami construct reduced the solid-state nanopore current to around 80% of its initial value. This is expected as counter ions in the vicinity of the DNA are mobile[23]. We see a consistent change in our experiments with solid-state nanopores with a range of diameters which points to a well-controlled insertion of the DNA origami structure.

Our results show that we can controllably and repeatedly insert and eject DNA origami constructs.

Detection of DNA with Hybrid Nanopores

We are able to detect λ-DNA strands in our hybrid nanopores. In this experiment DNA origami constructs with a concentration of 0.5 nM were added in addition to 1 nM of λ-DNA solution. As shown in FIG. 4a, we observe the typical signatures for long DNA molecules translocating a bare solid-state nanopore, indicating DNA forming a tight hairpin and folding onto itself[4a,24] After insertion of a DNA origami construct at 11.4 s (FIG. 4a), the current stabilizes after a few seconds albeit with a higher level of noise. Since the λ-DNA is present in the background, λ-DNA interactions with the hybrid nanopore will occur. Three typical events are presented for DNA translocations in FIG. 4b for the bare and hybrid nanopores, respectively. The corresponding current histograms are shown in FIG. 4c. We observe typical DNA translocation events as peaks in the bare solid-state pore current histogram (FIG. 4c) with peaks at −100 pA and −200 pA. The data is shown after the baseline was subtracted. The peaks indicate that DNA folding is readily observable in our bare solid-state nanopore prior to hybrid nanopore formation. For the hybrid nanopore current histogram, we observe a clear peak at roughly −60 pA, while we also detect a number of folded events although with lower frequency (FIGS. 4b and 4c). This can be explained by the considerably smaller diameter of the hybrid nanopore.

FIG. 5 shows schematically a complete testing cycle including: (a) the introduction of a DNA construct 1 having a sleeve formation 2 and tail formation 3 into a reservoir 4 on one side of a substrate 5 having a nanopore 6; (b) application of a positive polarity potential difference to thread the tail formation through the nanopore and thereby docking the construct to the substrate with the sleeve formation seated in the nanopore and the central aperture of the sleeve aligned with the nanopore; (c) testing of the current signature through the resulting hybrid nanopore when an analyte 7 is introduced into the reservoir; and (d) ejection of the construct on application of a negative polarity potential difference in readiness e.g. for the introduction of a different DNA construct into the reservoir and a further testing cycle.

CONCLUSIONS

We have experimentally demonstrated the formation of hybrid nanopores comprising 3D DNA origami structures inserted into a solid-state nanopore. The hybrid nanopores can be repeatedly assembled by reversing the applied potential, which enables the functionality of a nanopore sensor to be changed during an experiment. Our measurements of DNA detection show that DNA origami constructs can be used as resistive-pulse sensors. The constructs offer the possibility to adapt the diameter, shape and surface functionality of hybrid However, although the concept of construct insertion and expulsion has been demonstrated using a DNA construct, it could also be performed using constructs based on other suitable molecules. In particular, a molecular construct which, like DNA, can provide a hydrophilic external surface, may similarly help to prevent the construct from binding too tightly to the mating surface of the nanopore.

Further, although we have used a construct having a sleeve formation (which shows particular promise for stable docking and for controlling the functionality of the nanopore), other types of construct can be adopted. For example, FIG. 6 shows schematically (a) the introduction of a DNA construct 11 to a substrate 15 having a nanopore 16, the DNA construct having a body formation in the form of a flat plate 12 defining a central aperture 18, with a tail formation 13 extending from an edge of the aperture, and (b) the docking of the construct to the substrate, with the tail formation threaded through the aperture, the flat body formation overlaying the substrate, and the central aperture aligned with the nanopore.

Specific Analyte Detection

The approach described above involves measuring changes in ionic current as molecules translocate through the nanopore. Molecules of different type but similar molecular mass tend to generate similar changes in ionic current as the molecules translocate through the nanopore. Thus we next describe an approach which provides detection specificity for particular analytes.

More particularly, a molecular construct such as a DNA origami construct described above, can be used to trap an analyte of interest at the mouth of the nanopore by introducing one or more binding sites for the particular analyte at the aperture in the construct. Each time a construct is docked to the nanopore a current decrease due to the construct partially blocking the ionic current flow (FIG. 1) through the pore can be measured. However, when the analyte is present in the solution and therefore bound at the aperture, the current decrease is typically greater than when the analyte is absent from the solution.

This detection method can be adapted to many biomolecules of interest, such as antibodies, since it only requires the provision of binding sites on the construct, which in the case of DNA constructs can be achieved readily with oligonucleotide modifications offered by DNA synthesis companies.

The system is reversible. For example, in the case of DNA constructs and a SiN chip containing nanopores, a high positive voltage can be applied to dock the constructs to the pores and a high negative voltage can be applied to force them away from the pores. The step change in ionic current upon construct docking can be measured many times in one experiment (e.g. over hundreds of voltage reversals) to build up robust statistics. Further, since only a step change in current is being measured, low bandwidth electronics can be used.

As a proof of principle, a flat square DNA origami construct with a central aperture and four binding sites at the mouth of the aperture for the protein streptavidin was designed. A solution was prepared containing 0.5×TBE, 5.5 mM $MgCl_2$, 1M KCl. The constructs were then added to the solution, which was introduced to a SiN chip similar to those described above. A positive potential was applied to dock the constructs to the nanopores of the chip. Although the DNA constructs did not have tail formations, the apertures of the constructs were nonetheless able to align to the pores of the chips. FIGS. 7(a) and (b) show atomic force microscopy pictures of the docked constructs.

The procedure was then repeated but with streptavidin added to the solution. FIGS. 7(c) and (d) show atomic force microscopy pictures of the docked constructs, with bound streptavidin clearly visible at the apertures.

FIG. 8 shows schematically the change in ionic current that would be expected on docking of the constructs (a) from the solution without streptavidin and (b) from the solution with streptavidin. The expected decrease in current is greater for (b) than (a). The solution without streptavidin thus provides a reference decrease against which the decrease from a further solution which may contain streptavidin can be compared. If the decrease associated with the further solution differs from the reference by an amount similar to the amount by which (b) differs from (a), then that is an indication that the further solution contains streptavidin.

FIGS. 9(a) and (b) are histograms of percentage current decrease for actual experiments using the flat square DNA origami construct and streptavidin system of FIGS. 7(a) to (d). For the histogram of FIG. 9(a) the current decrease for the construct docking process using the reference system without any protein attached (FIGS. 7(a) and 7(b)) was repeatedly measured, whereas for the histogram of FIG. 9(b) the current decrease for the construct docking process using the system with the protein attached (FIGS. 7(c) and 7(d)) was repeatedly measured. As expected, the reference system shows a lower reduction in current than the system with the streptavidin bound to the construct. To ensure that the histograms were directly comparable, both the reference and the streptavidin-bound constructs were docked to the same nanopore-containing chip.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

All references are hereby incorporated by reference.

REFERENCES 1. (a) Dekker, C., Solid-state nanopores. *Nature Nanotechnology* 2007, 2 (4), 209-215; (b) Keyser, U. F., Controlling molecular transport through nanopores. *J R Soc Interface* 2011, 8 (63), 1369-1378.
2. Kasianowicz, J. J.; Brandin, E.; Branton, D.; Deamer, D. W., Characterization of individual polynucleotide molecules using a membrane channel. *Proceedings of the National Academy of Sciences of the United States of America* 1996, 93 (24), 13770-13773.
3. Li, J.; Stein, D.; McMullan, C.; Branton, D.; Aziz, M. J.; Golovchenko, J. A., Ion-beam sculpting at nanometre length scales. *Nature* 2001, 412 (6843), 166-169.
4. (a) Steinbock, L. J.; Otto, O.; Chimerel, C.; Gornall, J.; Keyser, U. F., Detecting DNA Folding with Nanocapillaries. *Nano Letters* 2010, 10 (7), 2493-2497; (b) Steinbock, L. J.; Otto, O.; Skarstam, D. R.; Jahn, S.; Chimerel, C.; Gornall, J. L.; Keyser, U. F., Probing DNA with micro- and nanocapillaries and optical tweezers. *Journal of Physics-Condensed Matter* 2010, 22 (45).
5. Storm, A. J.; Chen, J. H.; Ling, X. S.; Zandbergen, H. W.; Dekker, C., Fabrication of solid-state nanopores with single-nanometre precision. *Nat Mater* 2003, 2 (8), 537-540.
6. (a) Keyser, U. F.; Koeleman, B. N.; Van Dorp, S.; Krapf, D.; Smeets, R. M. M.; Lemay, S. G.; Dekker, N. H.; Dekker, C., Direct force measurements on DNA in a solid-state nanopore. *Nature Physics* 2006, 2 (7), 473-477; (b) Keyser, U. F.; van der Does, J.; Dekker, C.; Dekker, N. H., Optical tweezers for force measurements on DNA in nanopores. *Review of Scientific Instruments* 2006, 77 (10).
7. Peng, H. B.; Ling, X. S. S., Reverse DNA translocation through a solid-state nanopore by magnetic tweezers. *Nanotechnology* 2009, 20 (18).
8. McNally, B.; Singer, A.; Yu, Z. L.; Sun, Y. J.; Weng, Z. P.; Meller, A., Optical Recognition of Converted DNA Nucleotides for Single-Molecule DNA Sequencing Using Nanopore Arrays. *Nano Letters* 2010, 10 (6), 2237-2244.
9. Yusko, E. C.; Johnson, J. M.; Majd, S.; Prangkio, P.; Rollings, R. C.; Li, J. L.; Yang, J.; Mayer, M., Controlling protein translocation through nanopores with bio-inspired fluid walls. *Nature Nanotechnology* 2011, 6 (4), 253-260.
10. Wanunu, M.; Meller, A., Chemically modified solid-state nanopores. *Nano Letters* 2007, 7 (6), 1580-1585.
11. Hall, A. R.; Scott, A.; Rotem, D.; Mehta, K. K.; Bayley, H.; Dekker, C., Hybrid pore formation by directed insertion of alpha-haemolysin into solid-state nanopores. *Nature Nanotechnology* 2010, 5 (12), 874-877.
12. Clarke, J.; Wu, H. C.; Jayasinghe, L.; Patel, A.; Reid, S.; Bayley, H., Continuous base identification for single-molecule nanopore DNA sequencing. *Nature Nanotechnology* 2009, 4 (4), 265-270.
13. Branton, D.; Deamer, D. W.; Marziali, A.; Bayley, H.; Benner, S. A.; Butler, T.; Di Ventra, M.; Garaj, S.; Hibbs, A.; Huang, X. H.; Jovanovich, S. B.; Krstic, P. S.; Lindsay, S.; Ling, X. S. S.; Mastrangelo, C. H.; Meller, A.; Oliver, J. S.; Pershin, Y. V.; Ramsey, J. M.; Riehn, R.; Soni, G. V.; Tabard-Cossa, V.; Wanunu, M.; Wiggin, M.; Schloss, J. A., The potential and challenges of nanopore sequencing. *Nature Biotechnology* 2008, 26 (10), 1146-1153.
14. Seeman, N. C., Nanomaterials Based on DNA. *Annu Rev Biochem* 2010, 79, 65-87.
15. Rothemund, P. W. K., Folding DNA to create nanoscale shapes and patterns. *Nature* 2006, 440 (7082), 297-302.
16. (a) Douglas, S. M.; Dietz, H.; Liedl, T.; Hogberg, B.; Graf, F.; Shih, W. M., Self-assembly of DNA into nanoscale three-dimensional shapes. *Nature* 2009, 459 (7245), 414-418; (b) Dietz, H.; Douglas, S. M.; Shih, W. M., Folding DNA into Twisted and Curved Nanoscale Shapes. *Science* 2009, 325 (5941), 725-730; (c) Liedl, T.; Hogberg, B.; Tytell, J.; Ingber, D. E.; Shih, W. M., Self-assembly of three-dimensional prestressed tensegrity structures from DNA. *Nature Nanotechnology* 2010, 5

(7), 520-524; (d) Ke, Y. G.; Douglas, S. M.; Liu, M. H.; Sharma, J.; Cheng, A. C.; Leung, A.; Liu, Y.; Shih, W. M.; Yan, H., Multilayer DNA Origami Packed on a Square Lattice. *Journal of the American Chemical Society* 2009, 131 (43), 15903-15908; (e) Han, D. R.; Pal, S.; Nangreave, J.; Deng, Z. T.; Liu, Y.; Yan, H., DNA Origami with Complex Curvatures in Three-Dimensional Space. *Science* 2011, 332 (6027), 342-346.

17. (a) Jahn, K.; Torring, T.; Voigt, N. V.; Sorensen, R. S.; Bank Kodal, A. L.; Andersen, E. S.; Gothelf, K. V.; Kjems, J., Functional patterning of DNA origami by parallel enzymatic modification. *Bioconjug Chem* 2011, 22 (4), 819-23; (b) Jungmann, R.; Steinhauer, C.; Scheible, M.; Kuzyk, A.; Tinnefeld, P.; Simmel, F. C., Single-Molecule Kinetics and Super-Resolution Microscopy by Fluorescence Imaging of Transient Binding on DNA Origami. *Nano Letters* 2010, 10 (11), 4756-4761; (c) Pal, S.; Varghese, R.; Deng, Z. T.; Zhao, Z.; Kumar, A.; Yan, H.; Liu, Y., Site-Specific Synthesis and In Situ Immobilization of Fluorescent Silver Nanoclusters on DNA Nanoscaffolds by Use of the Tollens Reaction. *Angewandte Chemie-International Edition* 2011, 50 (18), 4176-4179; (d) Voigt, N. V.; Torring, T.; Rotaru, A.; Jacobsen, M. F.; Ravnsbaek, J. B.; Subramani, R.; Mamdouh, W.; Kjems, J.; Mokhir, A.; Besenbacher, F.; Gothelf, K. V., Single-molecule chemical reactions on DNA origami. *Nat Nanotechnol* 2010, 5 (3), 200-3; (e) Subramanian, H. K.; Chakraborty, B.; Sha, R.; Seeman, N. C., The label-free unambiguous detection and symbolic display of single nucleotide polymorphisms on DNA origami. *Nano Lett* 2011, 11 (2), 910-3.

18. Douglas, S. M.; Marblestone, A. H.; Teerapittayanon, S.; Vazquez, A.; Church, G. M.; Shih, W. M., Rapid prototyping of 3D DNA-origami shapes with caDNAno. *Nucleic Acids Research* 2009, 37 (15), 5001-5006.

19. Thorsen, T.; Maerkl, S. J.; Quake, S. R., Microfluidic large-scale integration. *Science* 2002, 298 (5593), 580-584.

20. Steinbock, L. J.; Stober, G.; Keyser, U. F., Sensing DNA-coatings of microparticles using micropipettes. *Biosens Bioelectron* 2009, 24 (8), 2423-2427.

21. Stein, I. H.; Schuller, V.; Bohm, P.; Tinnefeld, P.; Liedl, T., Single-Molecule FRET Ruler Based on Rigid DNA Origami Blocks. *Chemphyschem* 2011, 12 (3), 689-695.

22. (a) Siwy, Z. S., Ion-current rectification in nanopores and nanotubes with broken symmetry. *Adv Funct Mater* 2006, 16 (6), 735-746; (b) Siwy, Z.; Gu, Y.; Spohr, H. A.; Baur, D.; Wolf-Reber, A.; Spohr, R.; Apel, P.; Korchev, Y. E., Rectification and voltage gating of ion currents in a nanofabricated pore. *Europhysics Letters* 2002, 60 (3), 349-355.

23. Smeets, R. M. M.; Keyser, U. F.; Krapf, D.; Wu, M. Y.; Dekker, N. H.; Dekker, C., Salt dependence of ion transport and DNA translocation through solid-state nanopores. *Nano Letters* 2006, 6 (1), 89-95.

24. Li, J. L.; Gershow, M.; Stein, D.; Brandin, E.; Golovchenko, J. A., DNA molecules and configurations in a solid-state nanopore microscope. *Nat Mater* 2003, 2 (9), 611-615.

25. Voigt, N. V. et al., Single-molecule chemical reactions on DNA origami. *Nature nanotechnology* 2010, 5, 200-203.

The invention claimed is:

1. A DNA construct for docking to a substrate containing a nanopore of conical form through the substrate, the construct having a body formation which defines an aperture, and a tail formation extending from the body formation for threading through the nanopore to dock the construct to the substrate with the aperture and nanopore in alignment;
  wherein the body formation includes a sleeve formation which defines the aperture and which lines the nanopore when the construct is docked to the substrate, the sleeve formation having a tapered geometry for stable insertion into the nanopore, and wherein the tapered geometry of the sleeve formation is formed from staggered double helices forming overlapping skirts with the helices defining the central aperture.

2. The DNA construct according to claim 1, wherein the body formation is a DNA body formation.

3. A system comprising: a substrate containing one or more nanopores of conical form through the substrate, and one or more respective DNA constructs according to claim 1 which are docked to the one or more nanopores, the tail formation of each DNA construct threading through its nanopore to dock the DNA construct to the substrate with its aperture and the nanopore in alignment and with its sleeve formation lining the nanopore.

4. A method for determining the presence of an analyte, comprising the steps of:
  providing a system according to claim 3;
  measuring ionic current flow through the nanopores while translocating analyte molecules therethrough; and
  determining that the analyte molecules are present when a measured change in ionic current differs from a reference change in ionic current by a predetermined amount.

5. A method of controlling the functionality of a substrate containing at least one nanopore of conical form, the method including the steps of:
  introducing to the substrate a solution containing the DNA construct of claim 1;
  applying a potential difference across the substrate to thread the tail formation through the nanopore thereby docking the molecular construct to the substrate with the aperture aligned with the nanopore and with the sleeve formation stably inserted into and lining the nanopore; and
  expelling the molecular construct from the substrate by varying the potential difference.

6. The method according to claim 5, wherein the body formation has a docking surface which contacts the substrate when the construct is docked thereto, at least the docking surface being hydrophilic.

7. The method according to claim 5, wherein the molecular construct is a DNA construct.

8. The method according to claim 5, including further steps after the expelling step of:
  introducing to the substrate a solution containing a different molecular construct having a body formation which defines an aperture and a tail formation extending from the body formation, the body formation including a sleeve formation which defines the aperture and which has a tapered geometry; and
  re-applying a potential difference across the substrate to thread the tail formation through the nanopore thereby docking the different molecular construct to the substrate with the aperture aligned with the nanopore and with the sleeve formation stably inserted into and lining the nanopore.

9. A method of detecting the presence of an analyte in a solution, the method including the steps of:
  (a) providing a substrate containing at least one nanopore of conical form;

(b) introducing to the substrate a solution which may contain the analyte, and the DNA construct of claim 1, which has one or more binding sites for the analyte at the aperture;

(c) applying a potential difference across the substrate to dock the molecular construct to the substrate with the aperture aligned with the nanopore and with the sleeve formation stably inserted into and lining the nanopore, and measuring the corresponding change in ionic current through the nanopore;

(d) comparing the measured change in ionic current to a reference change in ionic current; and (e) determining that the analyte is present in the solution when the measured change in ionic current differs from the reference change in ionic current by more than a predetermined amount.

10. The method according to claim 9, wherein the applying step (c) includes repeatedly performing the sub-steps of:

(i) applying the potential difference across the substrate to dock the molecular construct to the substrate with the aperture aligned with the nanopore and with the sleeve formation stably inserted into and lining the nanopore, and measuring the corresponding change in ionic current through the nanopore; and (ii) expelling the molecular construct from the substrate by varying the potential difference; and wherein, in the comparing step (d), the measured change in ionic current is an average measured change derived from the repeated measurements of sub-step (c-i).

11. The method according to claim 9, further including the steps of:

(A) providing a substrate containing at least one nanopore having a conical form;

(B) introducing to the substrate a solution containing the molecular construct in the absence of the analyte; and (C) applying a potential difference across the substrate to dock the molecular construct, in the absence of the analyte, to the substrate with the aperture aligned with the nanopore and with the sleeve formation stably inserted into and lining the nanopore, and measuring the corresponding change in ionic current through the nanopore; and wherein, in the comparing step (d), the reference change in ionic current is the change in current measured at step (C).

12. The method according to claim 11, wherein the applying step (C) includes repeatedly performing the sub-steps of:

(i) applying the potential difference across the substrate to dock the molecular construct, in the absence of the analyte, to the substrate with the aperture aligned with the nanopore and with the sleeve formation stably inserted into and lining the nanopore, and measuring the corresponding change in ionic current through the nanopore; and (ii) expelling the molecular construct from the substrate by varying the potential difference; and wherein, in the comparing step (d), the reference change in ionic current is an average measured change derived from the repeated measurements of sub-step (C-i).

13. The method according to claim 9, wherein the analyte is an antibody.

14. The method according to claim 9, wherein the molecular construct is a DNA construct.

\* \* \* \* \*